United States Patent [19]
Balzer

[11] Patent Number: 5,965,502
[45] Date of Patent: *Oct. 12, 1999

[54] AQUEOUS VISCOELASTIC SURFACTANT SOLUTIONS FOR HAIR AND SKIN CLEANING

[75] Inventor: Dieter Balzer, Haltern, Germany

[73] Assignee: Huels Aktiengesellschaft, Marl, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/760,556

[22] Filed: Dec. 4, 1996

Related U.S. Application Data

[63] Continuation of application No. 08/431,728, May 1, 1995, abandoned.

[30] Foreign Application Priority Data

May 11, 1994 [DE] Germany .................. 44 16 566

[51] Int. Cl.$^6$ .................................................. C11D 1/83
[52] U.S. Cl. .......................... 510/158; 510/127; 510/403
[58] Field of Search ................................. 510/127, 158, 510/336, 351, 352, 357, 403, 427, 428, 469

[56] References Cited

U.S. PATENT DOCUMENTS

| | | | |
|---|---|---|---|
| 4,233,192 | 11/1980 | Lindemann et al. | 252/545 |
| 4,677,157 | 6/1987 | Jacobs | 524/789 |
| 4,752,409 | 6/1988 | Drapier et al. | 252/94 |
| 5,009,814 | 4/1991 | Kelkenberg et al. | 252/548 |
| 5,011,538 | 4/1991 | Smith | 134/22.13 |
| 5,055,219 | 10/1991 | Smith | 252/102 |
| 5,057,311 | 10/1991 | Kamegai et al. | 424/170 |
| 5,064,553 | 11/1991 | Dixit et al. | 252/94 |
| 5,100,573 | 3/1992 | Balzer | 252/174.17 |
| 5,217,637 | 6/1993 | Balzer . | |
| 5,284,603 | 2/1994 | Repinec, Jr. et al. | 252/546 |
| 5,393,450 | 2/1995 | Shana'a | 252/170 |
| 5,415,810 | 5/1995 | Lee et al. | 252/545 |
| 5,464,874 | 11/1995 | Balzer | 514/777 |
| 5,545,354 | 8/1996 | Ofusu-Asante | 510/237 |
| 5,629,278 | 5/1997 | Baeck | 510/236 |

OTHER PUBLICATIONS

D. Balzer, "Colloids And Surfaces", Elsevier, Physiochemical and Engineering Aspects, 99, (1995) 233–246.

*Primary Examiner*—Yogendra Gupta
*Assistant Examiner*—John R. Hardee
*Attorney, Agent, or Firm*—Oblon, Spivak, McClelland, Maier & Neustadt, P.C.

[57] ABSTRACT

Aqueous, viscoelastic surfactant solutions for the cleaning of hair and skin which contain:

(A) from 4 to 25% by weight of an anionic surfactant;
(B) from 0 to 10% by weight of a betainic surfactant;
(C) from 0 to 20% by weight of a nonionic surfactant;
(D) from 0 to 6% by weight of an electrolyte;
(E) from 0 to 5% by weight of a water-soluble polymer; and
(F) from 0 to 5% by weight of a further constituent; in which the sum of the amounts of (A), (B), and (C) is at least 10% by weight and the sum of the amounts of (C), (D), and (E) is between 2 and 20% by weight, in each case based on the total weight of the aqueous solution, and having a shear modulus, $G_0$, between 50 and 500 Pa at temperatures between 20 and 40° C. and a pH of from 4 to 8, and in which the conditions for the identity of the storage modulus, G', and the loss modulus, G", are in the angular frequency range between 0.1 and 60 rad·s$^{-1}$, exhibit optimum flow behavior for the intended applications.

11 Claims, 1 Drawing Sheet

AQUEOUS VISCOELASTIC SURFACTANT SOLUTIONS FOR HAIR AND SKIN CLEANING

This application is a Continuation of application Ser. No. 08/431,728, filed on May 1, 1995, now abandoned.

BACKGROUND OF THE INVENTION

1. Field of the Invention

The present invention relates to aqueous hair and skin cleaning compositions like shampoos, shower gels, bath gels or generally aqueous cosmetic cleaning liquids having high foaming ability, for which an increased viscosity is necessary or desired for application reasons.

2. Discussion of the Background

Aqueous hair and skin cleaning compositions have in the past been predominantly based on anionic surfactants, such as, in particular, fatty alcohol sulfates or fatty alcohol ether sulfates, if desired, in combination with fatty acid amides, i.e. surfactant combinations, which can be readily thickened by means of electrolytes. As alternatives, carbobetaines and sulfosuccinates have recently been included for reasons of higher skin compatibility. Suitable thickeners for these systems are likewise fatty alcohol ethoxylates having a relatively low degree of ethoxylation (see: A. Behler et al., S ÖFW, vol. 116, p. 60 (1990)) or alkyl polyglycosides (see: EP 0 070 074 and EP 0 384 983). Furthermore, in some cases water-soluble polymers are added as thickeners to the predominantly anionic surfactants.

In all of these formulations, only data on viscosity have entered into the discussion of the rheology in the literature; values and limitations for any elasticity present have, in contrast, not been mentioned.

Viscoelastic surfactant solutions (see: H. Hoffmann and H. Rehage, in *Surfactant Solutions, Surfactant Science Series*, vol. 22, R. Zana, Ed., New York, 1987, p. 209 ff.), i.e., systems which have both prominent viscous and elastic properties, which when supplied with mechanical energy therefore respond both with conversion into heat and storage of mechanical energy, have been studied primarily in the case of quaternary ammonium compounds in the presence of strongly binding counterions. The example of cetylpyridinium salicylate is typical. However, other cationic surfactants too, such as hexadecyltrimethylammonium bromide in the presence of extremely high salt concentrations, show viscoelastic behavior (see: A. Khatory et al, *Langmuir*, vol. 9, p. 1456 (1993)). Such properties of surfactants are used in special cleaners which are to be transported as undiluted by static water as possible to their site of action, such as, for example, low-surfactant, high-alkali and high-electrolyte pipe cleaners (see: EP 0 317 066). In other cases, the viscoelastic behaviour of cleaning solutions is enhanced by adding strongly crosslinked polymers which themselves are significantly elastic (see: EP 0 398 021 and EP 0 584 877). In the case of simple surfactant solutions, such as, in particular, the anionic surfactants which are so important in applications, viscoelastic behaviour has not hitherto been described. For the purposes of the present invention, surfactant solutions are liquids which can also contain dispersed materials.

The viscoelastic effects in the flow behaviour of aqueous personal care solutions have considerable importance for their use. Two processes in particular, namely taking the product from the container and its distribution on the skin or the hair, are relevant here. While the first process usually occurs at relatively low shear rates of up to about 10 $s^{-1}$, the distribution on the skin or the hair occurs under the action of substantially higher forces, usually at shear rates above 100 $s^{-1}$. The discussion which hitherto rested exclusively on viscosity data therefore promoted shear-thinning flow behaviour, by means of which slow flow from the container, simple metering combined with the effect of high active ingredient concentration, and also simple distribution on the skin are ensured. However, since shear-thinning surfactant systems frequently show viscoelastic effects and the elastic contributions usually increase strongly with rising forces, the discussion hitherto is insufficient and has to be corrected to take viscoelasticity into account. Accordingly, the elastic contributions must not become too high, since otherwise satisfactory distribution on the skin or the hair is made more difficult. In addition, high elasticity leads, during outflow of the liquid, to a relatively unappealing oscillation of the shapelessly thick liquid thread in the neck of the container; the liquid flows back if the inclination of the container is reduced only slightly. On the other hand, systems which are exclusively viscous tend to form very long rejuvenating threads, which in turn could form cobwebs, a behavior which is likewise very unsatisfactory aesthetically. Optimum flow behaviour of the liquid can therefore only be expected when viscosity and elasticity of the liquid are matched to one another.

Thus, there remains a need for aqueous viscoelastic surfactant solutions for hair and skin cleaning which exhibit good flow behavior and good distribution on the skin and hair.

SUMMARY OF THE INVENTION

Accordingly, it is one object of the present invention to discover the limits of the viscoelastic behaviour of surfactant solutions which ensure an optimum, i.e., desired by the consumer, flow behavior.

It is another object of the present invention to provide aqueous viscoelastic surfactant solutions which exhibit good flow behavior and good distribution on the skin and hair.

These and other objects, which will become apparent during the following detailed description, have been achieved by the inventor's discovery that solutions of from 4 to 25% by weight of an anionic surfactant together with from 0 to 10% by weight of a betainic surfactant and/or from 0 to 20% by weight of a nonionic surfactant and/or from 0 to 6% of an electrolyte and/or from 0 to 5% by weight of a water-soluble polymer and/or from 0 to 5% by weight of further constituents and composed in such a way that at temperatures between 20 and 40° C. and a pH of from 4 to 8 the shear modulus, $G_0$, of the solution is between 50 and 500 Pa and the conditions for the identity of storage modulus, G', and loss modulus, G", are in the angular frequency range between 0.1 and 60 rad·$s^{-1}$, exhibit the desired viscoelastic properties. Preference is given to those solutions in which $G_0$ is between 70 and 450 Pa and the conditions for the identity of G' and G" are in the angular frequency range from 0.3 to 50 rad·$s^{-1}$.

The present invention accordingly provides aqueous, viscoelastic surfactant solutions for the cleaning of hair and skin, which comprise:

(A) from 4 to 25% by weight of an anionic surfactant;
(B) from 0 to 10% by weight of a betainic surfactant;
(C) from 0 to 20% by weight of a nonionic surfactant;
(D) from 0 to 6% by weight of an electrolyte;
(E) from 0 to 5% by weight of a water-soluble polymer; and (F) from 0 to 5% by weight of further constituents, characterized in that the sum of the amounts of (A), (B), and (C) is at least 10% by weight and the sum of the amounts of (C), (D), and (E) is between 2 and 20% by weight, in each case based on the total weight of the aqueous solution, and in that at temperatures between 20 and 40° C. and a pH of from 4 to 8 the shear modulus, $G_0$, of the solution is between 50 and 500 Pa and the conditions for the identity of storage modulus, G', and loss modulus, G", are in the angular frequency range between 0.1 and 60 rad·s$^{-1}$.

Preferred amounts are (A), from 5 to 20% by weight; (B), from 0 to 8% by weight; (C), from 0 to 15% by weight; (D), from 0 to 5% by weight; and (E), from 0 to 4% by weight, where the sum of (C), (D) and (E) based on the total weight of the aqueous solution should be from 3 to 15% by weight.

The present invention further provides a process for the preparation of the present aqueous, viscoelastic surfactant solutions for the cleaning of hair and skin, comprising:

(A) from 4 to 25% by weight of an anionic surfactant;

(B) from 0 to 10% by weight of a betainic surfactant;

(C) from 0 to 20% by weight of a nonionic surfactant;

(D) from 0 to 6% by weight of an electrolyte;

(E) from 0 to 5% by weight of a water-soluble polymer; and (F) from 0 to 5% by weight of further constituents, said process comprising:

(i) selecting (A), (B), (C), (D), (E), and (F) on the basis of physical measurements such as that the sum of the amounts of (A), (B), and (C) is at least 10% by weight and the sum of the amounts of (C), (D), and (E) is between 2 and 20% by weight, in each case based on the total weight of said aqueous solution, and that at temperatures between 20 and 40° C. and a pH of from 4 to 8 the shear modulus, $G_0$, of the solution is between 50 and 500 Pa and the conditions for the identity of storage modulus, G', and loss modulus, G", are in the angular frequency range between 0.1 and 60 rad·s$^{-1}$.

It has now been observed that even aqueous fatty alcohol ether sulfate solutions have pronounced viscoelastic behaviour at concentrations conventional for personal care formulations in the presence of conventional amounts of electrolyte. This finding was likewise obtained in the case of mixtures of ether sulfates with other anionic surfactants or with betaines or with fatty alcohol ethoxylates. For combinations of fatty alcohol ether sulfates with alkyl polyglycosides, viscoelastic behaviour was also observed in some cases without electrolytes having to be added. The addition of typical polymers or other ingredients conventional in personal care formulations does not fundamentally change the viscoelastic behaviour, but usually only modifies it, the polymers being thought of here being not so much highly crosslinked polymers having extremely high molecular weights, but rather conventional chain molecules, in particular natural products or modified natural products.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawing, wherein.

DETAILED DESCRIPTION OF THE PREFERRED EMBODIMENTS

Figure 1:
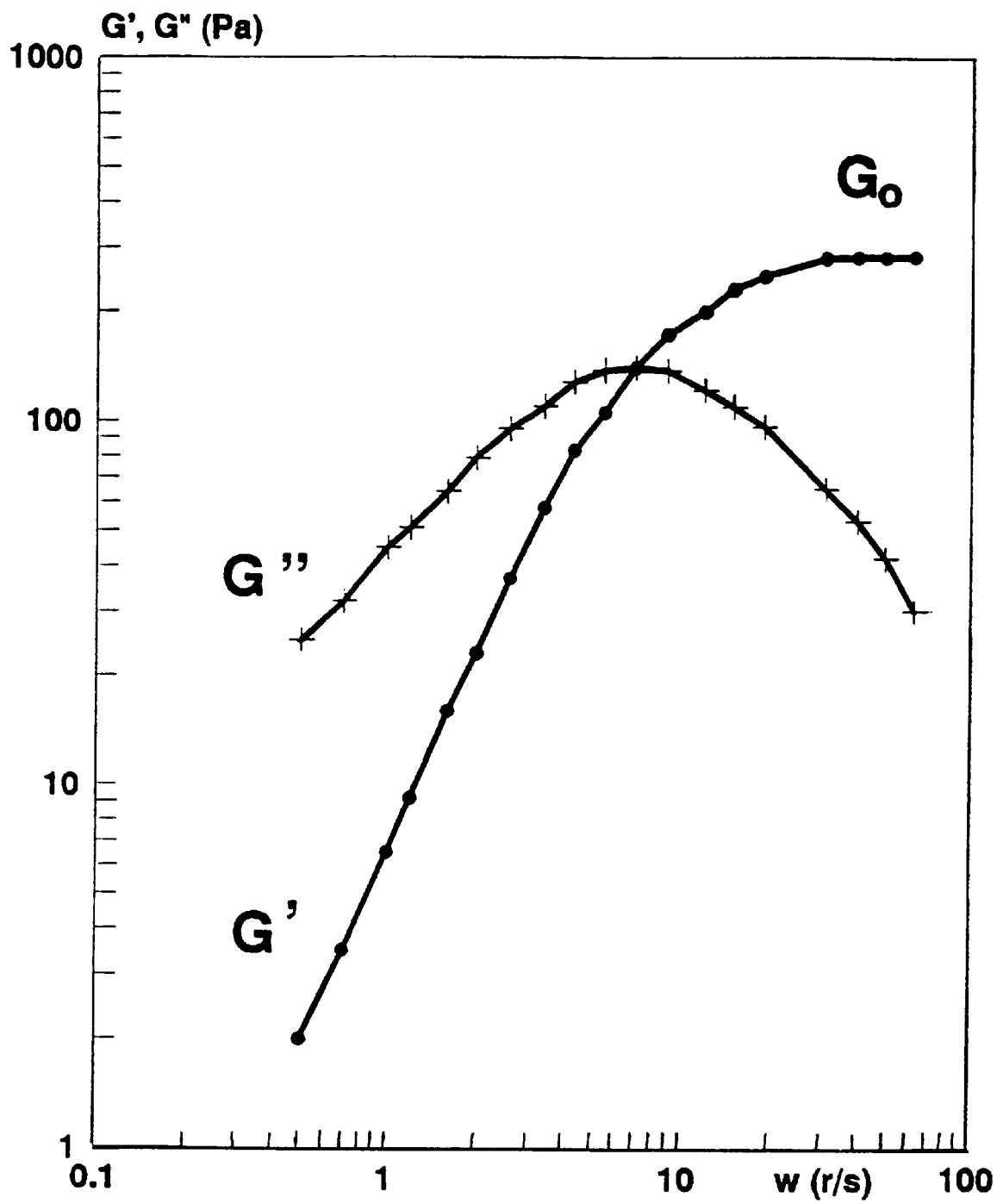
FIG. 1 is a graph of G' and G" as a function of the angular frequency for an aqueous solution of 15% by weight FAES and 5% by weight NaCl, amplitude 4 degrees.

The anionic surfactants used in the present invention are selected from the group consisting of fatty alcohol sulfates having from 10 to 18 carbon atoms in the alkyl group, fatty alcohol ether sulfates containing from 1 to 5 moles of ethylene oxide/mole and from 10 to 18 carbon atoms in the alkyl group, monoalkylethoxylate sulfosuccinates containing from 1 to 7 moles of ethylene oxide/mole and from 10 to 18 carbon atoms in the alkyl group, paraffinsulfonates based on $C_{12}$- to $C_{20}$-paraffins, phosphoric esters of $C_{10}$- to $C_{18}$-fatty alcohols, phosphoric esters of ethoxylated $C_{10}$- to $C_{18}$-fatty alcohols containing from 3 to 20 moles of ethylene oxide/mole, carboxymethylated $C_{10}$- to $C_{18}$-fatty alcohol ethoxylates containing from 2 to 20 moles of ethylene oxide/mole, $C_{10}$- to $C_{18}$-alkyl isethionates, $C_{12}$- to $C_{20}$-olefinsulfonates, and mixtures thereof. Particular preference is given to fatty alcohol ether sulfates. Preferred cations are alkali metal, ammonium, mono-, di-, tri, and tetra- $C_1$- to $C_3$-alkylammonium, or magnesium ions.

For the purposes of the present invention, betainic surfactants are alkyl betaines, alkylamido betaines and imidazoline betaines, all having at least one long-chain alkyl group of from 10 to 18 carbon atoms, and also mixtures thereof (see: J. Falbe, *Surfactants in Consumer Products*, London, 1987, p. 117 ff.). An example of an alkylamido betaine which may be mentioned is coconutamido propyl betaine.

The nonionic surfactants used in the present invention are selected from the group consisting of fatty alcohol ethoxylates, alkyl polyglycosides, fatty acid N-alkylpolyhydroxyamides, aminoxides, sorbitan esters, and mixtures thereof. The fatty alcohol ethoxylates here have the formula (I):

$$R\text{—}O\text{—}(CH_2\text{—}CH_2\text{—}O)_m\text{—}H, \qquad (I)$$

where R is a saturated or unsaturated, branched or unbranched alkyl radical having from 10 to 18 carbon atoms and m is a number between 1 and 8. For m, preference is given to numbers between 2 and 6.

The alkylpolyglycosides have the formula (II):

$$R'\text{—}O\text{—}Z_n, \qquad (II)$$

in which R' is saturated or unsaturated, branched or unbranched alkyl radical having from 10 to 16 carbon atoms and $Z_n$ is an oligoglycosyl radical consisting of from 1 to 3 hexose or pentose units or mixtures thereof. Preference is given to alkyl glucosides having degrees of glucosidification of between 1.1 and 2. Alkyl polyglucosides are very environmentally friendly new surfactants which have now, however, been well described (see EP 0 070 074 and EP 0 384 983, D. Balzer, *Tenside Surf. Det.*, vol. 28, p. 419 (1991), and D. Balzer, *Langmuir*, vol. 9, p. 3375 (1993)).

N-Alkyl polyhydroxy fatty acid amides have the formula (III):

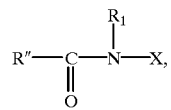

(III)

in which R" is a branched or unbranched alkyl radical having from 8 to 18 carbon atoms, $R_1$ is methyl, ethyl, n-, or i-propyl and X is a polyhydroxyhydrocarbyl radical having 4 to 6 carbon atoms and at least 3 hydroxy groups or mixtures thereof. Particularly preferred fatty acid N-alkylpolyhydroxyamides are fatty acid N-methylglucamides of the formula (IIIa)

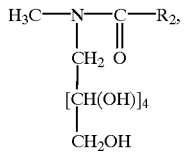

(IIIa)

in which $R_2$ is a branched or unbranched alkyl radical having from 10 to 16 carbon atoms.

The fatty acid N-alkylpolyhydroxyamides to be used according to the present invention can be prepared in a known manner by reaction of a fatty acid or fatty acid ester with an unsubstituted or N-substituted polyhydroxyalkylamine in the melt, in the presence or absence of an alkaline catalyst (see: EP 0 285 768).

Aminoxides used in the present invention have the formula (IV):

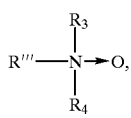

(IV)

in which R''' is a saturated or unsaturated, branched or unbranched alkyl radical having from 10 to 18 carbon atoms and $R_3$ and $R_4$ are short-chain $C_1$- to $C_3$-alkyl radicals.

Preference is given to $C_{12}$- to $C_{18}$-alkyldimethylaminoxides which can be prepared, for example, by $H_2O_2$-oxidation of the corresponding tertiary amines (see: DE 30 14 510).

Suitable sorbitan esters are sold, inter alia, by Atlas Powder Co. under the names SPAN® and TWEEN®.

Suitable electrolytes to be used in the present invention are all salts which are both toxicologically acceptable and are also compatible with the other constituents of the present compositions. These are preferably NaCl and $NH_4Cl$, but can also be $MgCl_2$, $Na_2SO_4$ and also alkali metal salts of carboxylic acids such as sodium citrate.

In the surfactant solutions of the present invention, water-soluble polymers serve to provide any desired advantageous, usually small, modification of the rheological profile which is essentially predetermined by the surfactant/electrolyte combination. Suitable polymers here are natural polysaccharides or their derivatives, such as xanthan, guar derivatives, sodium alginate, cellulose derivatives such as hydroxypropylcellulose or hydroxyethylcellulose, but also polyethylene oxides and polyacrylates. The number average molecular weight of these polymers is suitably between 200,000 and 3,000,000 g/mole. In the case of derivatives of polyethylene oxide or ethoxylated polyhydric alcohols in accordance with EP 0 511 466, lower molecular weight polymers are also present. These polymers or their mixtures are added in concentrations of up to 5% by weight, preferably up to 4% by weight, based on the total weight of the surfactant solution of the present invention.

Further constituents which may be used in the present surfactant solutions include conditioning agents (in particular cationic polymers such as, for example, cationic guar types or hydroxyethylcelluloses or also other cationic polymers as described in EP 0 337 354); quaternary surfactants, for example, of the long-chain alkyltrimethylammonium chloride type; silicone oils of the dimethylpolysiloxane type; oil-restoring substances such as glycerides of the MIGLYOL®, SOFTIGEN® or SOFTISAN® type; especially skin-compatible materials such as protein fatty acid condensates which can be prepared, for example, by reaction of plant or animal protein hydrolysates and fatty acid chlorides. The further constituents also include specific medically active compounds, buffer substances, preservatives and dyes. The remainder of the composition is water. The cleaning liquids of the invention are adjusted to a skin-friendly, usually weakly acid pH value.

The characteristic parameters according to the present invention for the respective system, $G_0$, and the structural relaxation time, $\tau$, or its reciprocal value, are obtained from equation (5) or (7), given below. Since G', even for non-Maxwell behaviour, tends towards a saturation value $G_0$ at higher frequencies, equation (5) is also valid for such systems.

The components of the aqueous surfactant solution according to the present invention are combined while stirring, if desired after prior dissolution in water and, after an equilibration time of at least 24 hours and carefully tested freedom from bubbles, are subjected to rheological examination. For this purpose, use is made of an oscillation viscometer (e.g. Haake CV 20) which allows the simultaneous determination of elastic and viscous contributions.

This requires the measurement to be carried out in the linear viscoelastic region which can be determined by means of a deformation test. Having thus determined the maximum amplitude, the oscillation of the cleaning solution is carried out at constant temperature over the entire frequency range. The storage modulus, G', is recorded as the elastic proportion, and the loss modulus, G", is recorded as the viscous proportion of the energy supplied to the system. It has been found that the aqueous surfactant solutions of the present invention behave in most cases as Maxwell liquids (see: H. Hoffmann and H. Rehage, in *Surfactant Solutions, Surfactant Science Series*, vol. 22, R. Zana, Ed., New York, 1987, p. 209 ff.) (cf. FIG. 1). Accordingly, $$G' = \frac{G_0 \omega^2 \tau^2}{1 + \omega^2 \tau^2} \text{ and} \tag{1}$$

$$G'' = \frac{G_0 \omega \cdot \tau}{1 + \omega^2 \tau^2} \tag{2}$$

where $\omega$ is the angular frequency (rad·s$^{-1}$), $\tau$ (s) is the structural relaxation time, and $G_0$ (Pa) is the shear modulus.

There are interesting limiting cases to consider:

At low frequencies, $\omega \cdot \tau < 1$:

$$G' \sim \omega^2 \tag{3}$$

$$G'' \sim \omega \tag{4}$$

and at high frequencies, $\omega \cdot \tau > 1$:

$$G' \approx G_0. \tag{5}$$

In the case G'=G":

$$G_0 = 2G'; \text{ and} \tag{6}$$

$$\tau = 1/\omega, \tag{7}$$

where $\tau$ is the structural relaxation time of the liquid.

The present surfactant solutions may be prepared by mixing the various components either before or after diluting with water. The resulting surfactant solutions can be used to clean the hair and/or skin by applying an appropriate amount of the surfactant solution to the hair and/or skin for a time sufficient to clean the hair and/or skin and then rinsing with water.

Other features of the invention will become apparent in the course of the following descriptions of exemplary embodiments which are given for illustration of the invention and are not intended to be limiting thereof.

EXAMPLES

The solutions in the following Table were prepared by mixing the components in the amount indicated in the Table. All amounts are given in weight %, based on the total weight of the solution, and water was present in each solution in an amount sufficient to make the total of the amounts for each solution sum to 100% by weight.

The solutions were adjusted to pH 6 and measured rheologically at 25° C. Besides examples predominantly according to the invention, the table also contains some comparative examples corresponding to cleaning liquids having unsatisfactory rheological properties, either because they have an elastic contribution which is too small (Examples 2 and 5) or because their ω value is too high (Example 20) or too low (Example 18).

The abbreviations used in the table below have the following meanings:

FAES: $C_{12}$-$C_{14}$-fatty alcohol ether sulfate sodium salt containing 2 moles of ethylene oxide/mole;
FAECM: carboxymethylated $C_{12}$-$C_{14}$-fatty alcohol ethoxylate sodium salt containing 4.5 moles of ethylene oxide/mole;
FASS: $C_{12}$-$C_{14}$-fatty alcohol ethoxylate sulfosuccinate sodium salt containing 3 moles of ethylene oxide/mole;
Betaine: $C_{12}$-$C_{14}$-fatty acid amidopropylbetaine;
FAE: $C_{12}$-$C_{14}$-fatty alcohol ethoxylate containing 3 moles of ethylene oxide/mole;
alkyl polyglycoside(s): $C_{12}$-$C_{14}$-alkyl polyglucoside having a degree of glucosidification of 1.2;
FAGA: $C_{12}$-fatty acid N-methylglucamide;
PEG: POLYOX® resin WSR N-60 K, Union Carbide;
Guar derivative: JAGUAR® HP 60, Meyhall;
Xanthan: KELTROL® T, Kelco;
Silicone oil: AK 100, Wacker;
JR 400: UCARE® JR 400 from Amercol;
Protein fatty acid condensate: LAMEPON® S, Henkel; and
SOFTIGEN® 767: Ethoxylated caprylic-capric acid partial glyceride, Hüls AG.

TABLE

| Component | Example | | | | | |
|---|---|---|---|---|---|---|
| | 1 | 2(V) | 3 | 4 | 5(V) | 6 |
| (1st part) | | | | | | |
| FAES | 15 | 15 | 14 | 17 | 23 | 6 |
| FAECM | — | — | — | — | — | — |
| FASS | — | — | — | — | — | — |
| BETAINE | — | — | — | — | — | — |
| FAE | — | — | 3.5 | 4 | 6 | — |
| alkyl polyglycoside(s) | — | — | — | — | — | 19 |
| FAGA | — | — | — | — | — | — |
| NaCl | 5 | 2 | 2 | 2 | 3 | — |
| PEG | — | — | — | — | — | — |
| Guar | — | — | — | — | — | — |
| Xanthan | — | — | — | — | — | — |
| Silicone oil | — | — | — | — | — | — |
| JR 400 | — | — | — | — | — | — |
| Protein fatty acid condensate | — | — | — | — | — | — |
| SOFTIGEN® 767 | — | — | — | — | — | — |
| $G_O$ max (Pa) | 280 | ≈10 | 280 | 400 | — | 400 |
| $\omega_{G'=G''}$ (rad.s$^{-1}$) | 7 | 142 | 14 | 18 | 130 | 23 |

| | 7 | 8 | 9 | 10 | 11 | 12 |
|---|---|---|---|---|---|---|
| (2nd part) | | | | | | |
| FAES | 4 | 7.5 | 8.5 | 10 | 7.5 | 10 |
| FAECM | — | — | 3.0 | — | — | — |
| FASS | — | — | — | — | 7.5 | — |
| BETAINE | — | — | — | 2 | — | 2 |
| FAE | — | — | — | — | — | — |
| alkyl polyglycoside(s) | 13 | 7.5 | 8.5 | 5 | — | — |
| FAGA | — | — | — | — | 2 | 5 |
| NaCl | — | 2 | 2 | 1 | 4 | — |
| PEG | — | — | — | — | — | — |
| Guar | — | — | — | — | — | — |
| Xanthan | — | — | — | — | — | — |
| Silicone oil | — | — | — | — | — | — |
| JR 400 | — | — | — | — | — | — |
| Protein fatty acid condensate | — | — | — | — | — | — |
| SOFTIGEN® 767 | — | — | — | — | — | — |
| $G_O$ max (Pa) | 100 | 180 | 200 | 180 | 110 | 160 |
| $\omega_{G'=G''}$ (rad.s$^{-1}$) | 15 | 20 | 22 | 24 | 43 | 22 |

| | 13 | 14 | 15 | 16 | 17 | 18(V) |
|---|---|---|---|---|---|---|
| (3rd part) | | | | | | |
| FAES | 12 | 5 | 7.5 | 7.5 | 7.5 | 15 |
| FAECM | — | — | — | — | — | — |
| FASS | — | — | — | — | — | — |
| BETAINE | 5 | 2 | — | — | — | — |
| FAE | — | — | — | — | — | — |
| alkyl polyglycoside(s) | — | — | 7.5 | 7.5 | 7.5 | — |
| FAGA | — | 10 | — | — | — | — |
| NaCl | 3 | — | 1 | 2 | 2 | 0.5 |
| PEG | — | — | — | — | — | — |
| Guar | — | — | — | — | — | 2.5 |
| Xanthan | — | — | 1 | — | — | — |
| Silicone oil | — | — | — | — | — | — |
| JR 400 | — | — | — | 2 | 2 | — |
| Protein fatty acid condensate | — | — | — | — | 1 | — |
| SOFTIGEN® 767 | — | — | — | — | — | — |
| $G_O$ max (Pa) | 200 | 400 | 80 | 300 | 320 | 230 |
| $\omega_{G'=G''}$ (rad.s$^{-1}$) | 5 | 25 | 50 | 6 | 34 | 0.02 |

| | 19 | 20(V) | 21 | 22 | 23 |
|---|---|---|---|---|---|
| (4th part) | | | | | |
| FAES | 15 | 15 | 10 | 10 | 8 |
| FAECM | — | — | 7 | 7 | — |
| FASS | — | — | — | — | — |
| BETAINE | — | — | 2 | 2 | 4 |
| FAE | — | — | — | — | — |
| alkyl polyglycoside(s) | — | — | — | — | 4 |
| FAGA | — | — | — | — | 1 |
| NaCl | 0.5 | 0.5 | 2.8 | 2.8 | 2 |
| PEG | — | 1.5 | — | — | — |
| Guar | 1.5 | — | — | — | — |
| Xanthan | — | — | — | — | — |
| Silicone oil | — | — | — | — | — |
| JR 400 | — | — | — | — | 1 |
| Protein fatty acid condensate | — | — | 2 | 2 | 2 |
| SOFTIGEN® 767 | — | — | — | — | 1 |

TABLE-continued

| Component | Example | | | | |
|---|---|---|---|---|---|
| $G_O$ max (Pa) | 140 | 100 | 175 | 200 | 200 |
| $\omega_{G'=G''}$ (rad.s$^{-1}$) | 1 | 60 | 50 | 7 | 41 |

This application is based on German Patent Application P 44 16 566.8 filed May 11, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. An aqueous, viscoelastic surfactant solution for the cleaning of hair and skin, consisting essentially of
   (A) from 4 to 25% by weight of an anionic surfactant selected from the group consisting of fatty alcohol sulfates having from 10 to 18 carbon atoms in the alkyl group, fatty alcohol ether sulfates containing from 1 to 5 moles of ethylene oxide/mole and from 10 to 18 carbon atoms in the alkyl group, monoalkylethoxylate sulfosuccinates containing from 1 to 7 moles of ethylene oxide/mole and from 10 to 18 carbon atoms in the alkyl group, paraffinsulfonates having from 12 to 20 carbon atoms in the alkyl group, phosphoric esters of $C_{10}$- to $C_{18}$-fatty alcohols, phosphoric esters of ethoxylated $C_{10}$- to $C_{18}$-fatty alcohols, $C_{10}$- to $C_{18}$-alkyl isethionates, olefinsulfonates having from 10 to 20 carbon atoms in the alkyl or alkylene groups, and mixtures thereof, with a counterion selected from the group consisting of alkali metals, ammonium, mono-, di-, tri-, and tetra-$C_1$- to $C_3$-alkylammonium, and Mg;
   (B) from 0 to 10% by weight of a betainic surfactant selected from the group consisting of alkylamido betaines, alkyl betaines, imidazoline betaines, in each case having from 10 to 18 carbon-atoms in the alkyl group, and mixtures thereof;
   (C) from 0 to 20% by weight of a nonionic surfactant;
   (D) from 0 to 6% by weight of an electrolyte selected from the group consisting of alkali metal chlorides, ammonium chlorides, magnesium chloride, alkali metal sulfates, alkali metal carboxylates, and mixtures thereof,
   (E) from 0 to 5% by weight of a water-soluble polymer selected from the group consisting of polysaccharides of the xanthan or guar type, derivatives thereof, cellulose derivatives, polyethylene oxides and polyacrylates; and
   (F) from 0 to 5% by weight of a further constituent; wherein the sum of the amounts of (A), (B), and (C) is at least 10% by weight and the sum of the amounts of (C), (D), and (E) is between 2 and 20% by weight, in each case based on the total weight of said aqueous solution, and wherein at a temperature between 20 and 40° C. and a pH of from 4 to 8, said solution exhibits a shear modulus, $G_0$, between 50 and 500 Pa and the conditions for identity of storage modulus, G', and loss modulus, G", are in an angular frequency range between 0.1 and 60 rad·s$^{-1}$, wherein said solution does not contain a fatty acid N-alkylpolyhydroxyamide.

2. The aqueous, viscoelastic surfactant solution of claim 1, wherein at temperatures between 20 and 40° C. and a pH of from 4 to 8 said shear modulus, $G_0$, of said solution is between 70 and 450 Pa and said conditions for said identity of G' and G" are in the an angular frequency range between 0.3 and 50 rad·s$^{-1}$.

3. The aqueous, viscoelastic surfactant solution of claim 1, wherein said nonionic surfactant is selected from the group consisting of fatty alcohol ethoxylates, alkyl polyglucosides, fatty acid N-alkylpolyhydroxyamides, aminoxides, sorbitan esters, and mixtures thereof.

4. The aqueous, viscoelastic surfactant solution of claim 3, wherein said fatty alcohol ethoxylate has the formula (I):

$$R\text{—}O\text{—}(CH_2\text{—}CH_2\text{—}O)_m\text{—}H, \quad (I)$$

wherein R is a saturated or unsaturated, branched or unbranched alkyl radical having from 10 to 18 carbon atoms and m is a number between 1 and 8.

5. The aqueous, viscoelastic surfactant solution of claim 3, wherein said alkylpolyglycoside has the formula (II):

$$R'\text{—}O\text{—}Z_n, \quad (II)$$

wherein R' is a saturated or unsaturated, branched or unbranched alkyl radical having from 10 to 16 carbon atoms and $Z_n$ is an oligoglycosyl radical consisting of from 1 to 3 hexose or pentose units or mixtures thereof.

6. The aqueous, viscoelastic surfactant solution of claim 3, wherein said alkylaminoxide has the formula (IV)

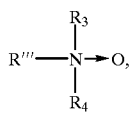

(IV)

wherein R''' is a saturated or unsaturated, branched or unbranched alkyl radical having from 10 to 18 carbon atoms and $R_3$ and $R_4$ are methyl, ethyl, n-, or i-propyl.

7. The aqueous, viscoelastic surfactant solution of claim 1, wherein said water-soluble polymer has a number average molecular weight between 200,000 and 3,000,000 g/mole.

8. The aqueous, viscoelastic surfactant solution of claim 1, wherein said further constituent is selected from the group consisting of oil restorers, conditioning agents, medical active ingredients, buffer substances, dyes, perfumes and preservatives.

9. The aqueous, viscoelastic surfactant solution as claimed in claim 1, wherein said nonionic surfactant (C) is a member selected from the group consisting of fatty alcohol ethoxylates, alkyl polyglucosides, aminoxides, sorbitan esters and mixtures thereof.

10. A process for preparing an aqueous, viscoelastic surfactant solution for the cleaning of hair and skin, said solution comprising:
   (A) from 4 to 25% by weight of an anionic surfactant selected from the group consisting of fatty alcohol sulfates having from 10 to 18 carbon atoms in the alkyl group, fatty alcohol ether sulfates containing from 1 to 5 moles of ethylene oxide/mole and from 10 to 18 carbon atoms in the alkyl group, monoalkylethoxylate sulfosuccinates containing from 1 to 7 moles of ethylene oxide/mole and from 10 to 18 carbon atoms in the alkyl group, paraffinsulfonates having from 12 to 20 carbon atoms in the alkyl group, phosphoric esters of $C_{10}$- to $C_{18}$-fatty alcohols, phosphoric esters of ethoxylated $C_{10}$- to $C_{18}$-fatty alcohols, $C_{10}$- to $C_{18}$-alkyl isethionates, olefinsulfonates having from 10 to 20 carbon atoms in the alkyl or alkylene groups, and mixtures thereof, with a counterion selected from the group consisting of alkali metals, ammonium, mono-, di-, tri-, and tetra-$C_1$- to $C_3$-alkylammonium, and Mg;

(B) from 0 to 10% by weight of a betainic surfactant;

(C) from 0 to 20% by weight of a nonionic surfactant;

(D) from 0 to 6% by weight of an electrolyte;

(E) from 0 to 5% by weight of a water-soluble polymer; and (F) from 0 to 5% by weight of one or more further constituents; said process comprising:

(i) selecting (A), (B), (C), (D), (E), and (F) on the basis of physical measurements such that the sum of the amounts of (A), (B), and (C) is at least 10% by weight and the sum of the amounts of (C), (D), and (E) is between 2 and 20% by weight, in each case based on the total weight of the aqueous solution, and wherein at a temperature between 20 and 40° C. and a pH of from 4 to 8, said solution exhibits a shear modulus, $G_0$, between 50 and 500 Pa and the conditions for identity of storage modulus, G', and loss modulus, G", are in an angular frequency range between 0.1 and 60 rad·$s^{-1}$ wherein said solution does not contain a fatty acid N-alkylpolyhydrioyamide; and (ii) mixing said components (A), (B), (C), (D), (E), and (F).

11. A method of cleaning hair or skin, comprising:

(i) contacting hair or skin with a composition comprising:

(A) from 4 to 25% by weight of an anionic surfactant selected from the group consisting of fatty alcohol sulfates having from 10 to 18 carbon atoms in the alkyl group, fatty alcohol ether sulfates containing from 1 to 5 moles of ethylene oxide/mole and from 10 to 18 carbon atoms in the alkyl group, monoalkylethoxylate sulfosuccinates containing from 1 to 7 moles of ethylene oxide/mole and from 10 to 18 carbon atoms in the alkyl group, paraffinsulfonates having from 12 to 20 carbon atoms in the alkyl group, phosphoric esters of $C_{10}$- to $C_{18}$-fatty alcohols, phosphoric esters of ethoxylated $C_{10}$- to $C_{18}$-fatty alcohols, $C_{10}$- to $C_{18}$-alkyl isethionates, olefinsulfonates having from 10 to 20 carbon atoms in the alkyl or alkylene groups, and mixtures thereof, with a counterion selected from the group consisting of alkali metals, ammonium, mono-, di-, tri-, and tetra-$C_1$- to $C_3$-alkylammonium, and Mg;

(B) from 0 to 10% by weight of a betainic surfactant;

(C) from 0 to 20% by weight of a nonionic surfactant;

(D) from 0 to 6% by weight of an electrolyte;

(E) from 0 to 5% by weight of a water-soluble polymer; and (F) from 0 to 5% by weight of a further constituent; wherein the sum of the amounts of (A), (B), and (C) is at least 10% by weight and the sum of the amounts of (C), (D), and (E) is between 2 and 20% by weight, in each case based on the total weight of said aqueous solution, and wherein at a temperature between 20 and 40° C. and a pH of from 4 to 8, said solution exhibits a shear modulus, $G_0$, between 50 and 500 Pa and the conditions for identity of storage modulus, G', and loss modulus, G", are in an angular frequency range between 0.1 and 60 rad·$s^{-1}$ wherein said composition does not contain a fatty acid N-alkylpolyhydroxyamide;

for a time sufficient to effect the cleaning of said hair or skin; and (ii) rinsing said composition from said hair or skin with water.

* * * * *